United States Patent
Haber et al.

[11] Patent Number: 5,304,128
[45] Date of Patent: Apr. 19, 1994

[54] GAS POWERED SELF CONTAINED SYRINGE

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 949,168

[22] Filed: Sep. 22, 1992

[51] Int. Cl.⁵ .............................................. A61M 5/30
[52] U.S. Cl. ........................................ 604/68; 604/70; 604/143; 604/49
[58] Field of Search .................................. 604/68-70, 604/140, 141, 143, 144, 146

[56] References Cited

U.S. PATENT DOCUMENTS

| | | | |
|---|---|---|---|
| 4,089,334 | 3/1978 | Schwebel et al. | 604/69 |
| 4,561,856 | 12/1985 | Cochran | 604/143 |
| 4,640,445 | 2/1987 | Yamada | 604/145 |
| 4,969,874 | 11/1990 | Michel et al. | 604/141 |
| 5,009,637 | 4/1991 | Newman et al. | 604/68 |
| 5,064,413 | 11/1991 | McKinnon et al. | 604/70 |

Primary Examiner—C. Fred Rosenbaum
Assistant Examiner—Michael Rafa
Attorney, Agent, or Firm—Townsend & Townsend Khourie & Crew

[57] ABSTRACT

The present invention is directed to a syringe that includes a gas driven piston to force liquid medication from a syringe cartridge through a variety of injection nozzles. The syringe may be mechanically operated for loading or aspirating the syringe.

14 Claims, 8 Drawing Sheets

GAS POWERED SELF CONTAINED SYRINGE

BACKGROUND OF THE INVENTION

The present invention is directed to a syringe that includes a gas driven piston to force liquid medication from a syringe cartridge through a variety of injection nozzles. The nozzles include a traveling hidden needle which is retracted until the syringe is activated and then is extended to puncture the skin of the person injected. The invention also contemplates a needleless injection nozzle which will permit injection without a needle. Further, in accordance with the invention, a very short needle which only barely penetrates the skin to assist injection is provided. The syringe may be mechanically operated for loading or aspirating the syringe.

The use of needleless injection has two major advantages. First, there is a needle phobia that is astonishingly widespread. Therefore, an injector that doesn't use or present a needle can do a lot to dispel that stigma from a lot of people. Secondly, the use of needleless injection decreases the frequency of accidental needle sticking and thus reduce the risk of the spread of possibly disease among the people who would otherwise handle the used needle. Use of needleless injection reduces tissue trauma and the development of scar tissue.

Needleless injection is well known in the art. In World War II for example, there are stories about lines of soldiers who were given pneumatically aspirated needleless injections. This was done for mass production reasons of getting the most injections in the most people in the least amount of time. The injectors used were massive guns. These guns utilized compressed air of maybe 500 psi and therefore needed substantial pressure chamber or accumulation chambers in order to provide sufficient energy to drive the liquid medication or vaccine through the skin.

The art has recognized the advantages of needleless injection. For example, the Russian literature recognized that Soviet needleless injectors were used in anesthetic practice with 271 patients (1670 injections) for premedication, local anesthesia in all sorts of surgical procedures, in primary surgical treatment of wounds, in bone fractures and for administration of analgesics during the postoperative period. Effects supervened 2-3 times more rapidly and the doses were 2-5 times smaller than when an ordinary syringe with a needle was used. Needleless injectors have definite advantages over syringes.

Further, the German literature has noted that when looking for new techniques of insulin applications which could replace the insulin syringe, we examined the possibility of using a dosable jet injector (Med. E Jet Injector) for dosing precision and handling as well as for bioavailability of insulin by measuring plasma insulin and blood glucose effects whereby syringe injection and jet injection were compared. In the following, we tested the compatibility of this latter type of application. Jet injection of insulin turned out to be more precise and compatibility at the site of a single test was good. The insulin appeared faster in the blood and accordingly disappeared faster after application of regular insulin (Alt-Insulin CS, Hoechst) and of crystalline intermediate acting insulin (Monotard MC, Novo) or of acid intermediate acting insulin (Depotinsulin CS, Hoechst). Blood glucose and C-peptide as a measure of B-cell function inhibition decreased more rapidly. This fact points to a faster kinetic after insulin jet injection. Hence, the jet injection technique is basically suited for insulin application. When changing over from syringe to jet injection differences in kinetics have to be considered.

Thus, the art has recognized both the advantages and the benefits that are gained through the use of needleless injection. There are known needleless injectors with many different mechanical methods of operation. For example, there are commercially available needleless insulin injectors that use spring power to provide the injection force. These devices generally require complicated manipulation before they are ready to use. There is still a need for a self-contained compact versatile injection syringe that can be used to give an individual injection utilizing a needleless injection nozzle and be used to give injections with minimum needle exposure and use.

SUMMARY OF THE INVENTION

In a broad aspect, the present invention is directed to a gas powered self contained syringe that includes a gas driven piston to force liquid medication from a syringe cartridge through a variety of nozzles. The nozzles include a traveling hidden needle which is retracted until the syringe is activated and then is extended to puncture the skin of the person injected. The invention contemplates a needleless injection nozzle which will permit injection without a needle. Further, in accordance with the invention, a very short needle which only barely penetrates the skin to assist injection is provided. A stem and a handle are disconnectably connected to the gas driven piston so that the syringe of the present invention may also be mechanically operated.

The invention is directed to a syringe including a piston housing having distal and proximal ends. A piston is located in the piston housing and is adapted for reciprocal movement. The piston has an elongated portion including a stopper at its lower end. The elongated portion extends out of the distal end of the piston housing. The elongated portion is sized to be inserted into a syringe cartridge and is preferably coaxially arranged with the piston. A power cap is positioned on the proximal end of the piston housing. A gas producing means is located in the power cap adjacent to the proximal end of the piston housing for driving the piston down the piston housing. A means for activating the gas producing means is located adjacent to the gas producing means.

More particularly, the syringe includes a piston housing having distal and proximal ends. A syringe cartridge is attached to the distal end of the piston housing coaxially aligned with the piston. An injection nozzle is disconnectably connected to the syringe cartridge. A piston is located in the piston housing and adapted for reciprocal movement therein. There is a central opening in the piston. A tubular elongated portion extends out of the lower end of the piston housing into the syringe cartridge. On activation of a power source the elongated portion is adapted to expel medication from the cartridge. A power cap is attached to the proximal end of the piston housing and also has a central opening. A stem passes in sealing engagement through the central opening in the power cap and the central opening in the piston. The stem is disconnectably connectable to the piston for moving the piston in the piston housing and the elongated portion in the syringe cartridge. A reagent capable of rapid gassification when activated is located in the power cap adjacent to the proximal end of the piston housing for driving the piston down the piston chamber and the elongated portion down the syringe cartridge to eject medication therefrom. Activating means are provided for converting the reagent to high pressure gas to result in expelling the medication from the syringe cartridge.

The invention also contemplates a method of giving an injection to a person. A syringe cartridge is connected to the distal end of a syringe. A syringe stem is disconnectably connected to a piston located in a piston housing of the syringe. The operator then loads the syringe cartridge with medication by extending the syringe stem out of the proximal end of the piston housing. After the syringe cartridge is filled the desired amount, the stem is disconnected from the piston and the syringe is placed against the desired location of the person to be injected and gas is caused to expand in the piston housing to drive the piston toward the loaded syringe cartridge whereby medication is expelled from the cartridge and injected into the desired location of the person to be injected.

OBJECTS OF THE INVENTION

It is a particular object of the present invention to provide a gas driven self contained syringe which may utilize a variety of injection nozzles including a needleless nozzle. It is a further object of the present invention to provide a syringe which contains a reagent which, when activated, will gassify to drive a plunger into a syringe cartridge to expel medication therefrom. It is also an object of the present invention to provide a syringe that can be mechanically operated to load or aspirate the syringe and is gas operated to provide rapid high pressure needleless injection. Additional objects and advantages of the present invention will become apparent from the following description read in view of the accompanying drawings, which are made a part of this specification.

BRIEF DESCRIPTION OF THE DRAWINGS

FIG. 5 is an enlarged section view and illustrates the preferred form of an injection nozzle for use in withdrawing medication from a vial or the like;

DESCRIPTION OF THE PREFERRED EMBODIMENT

The syringe of the present invention is best described while referring to the drawings and, in particular, to FIGS. 1-4. The syringe includes a piston housing 20 having a proximal end 22 and a distal end 24. A piston 26 is located in the piston housing 20 and is adopted to move reciprocally therein. The piston has an o-ring 28 to sealingly engage it in the piston housing 20. Air vents 8, 9 are provided in the distal end of piston housing 20 to allow exhaust. The piston 26 has an elongated portion 30 which extends out of the distal end 24 of the piston housing 20. Preferably the diameter of the piston 26 should be at least three times the diameter of the elongated portion.

The tubular elongated portion 30 has a stopper 32 and a suitable o-ring 34 which is adapted to be inserted into a syringe cartridge 36 for expelling medication from the cartridge. They syringe cartridge 36 is attached to the distal end 24 of the piston housing by suitable means such as mating threads 38 and 39 on the piston housing and the syringe cartridge respectively.

Figure 4:
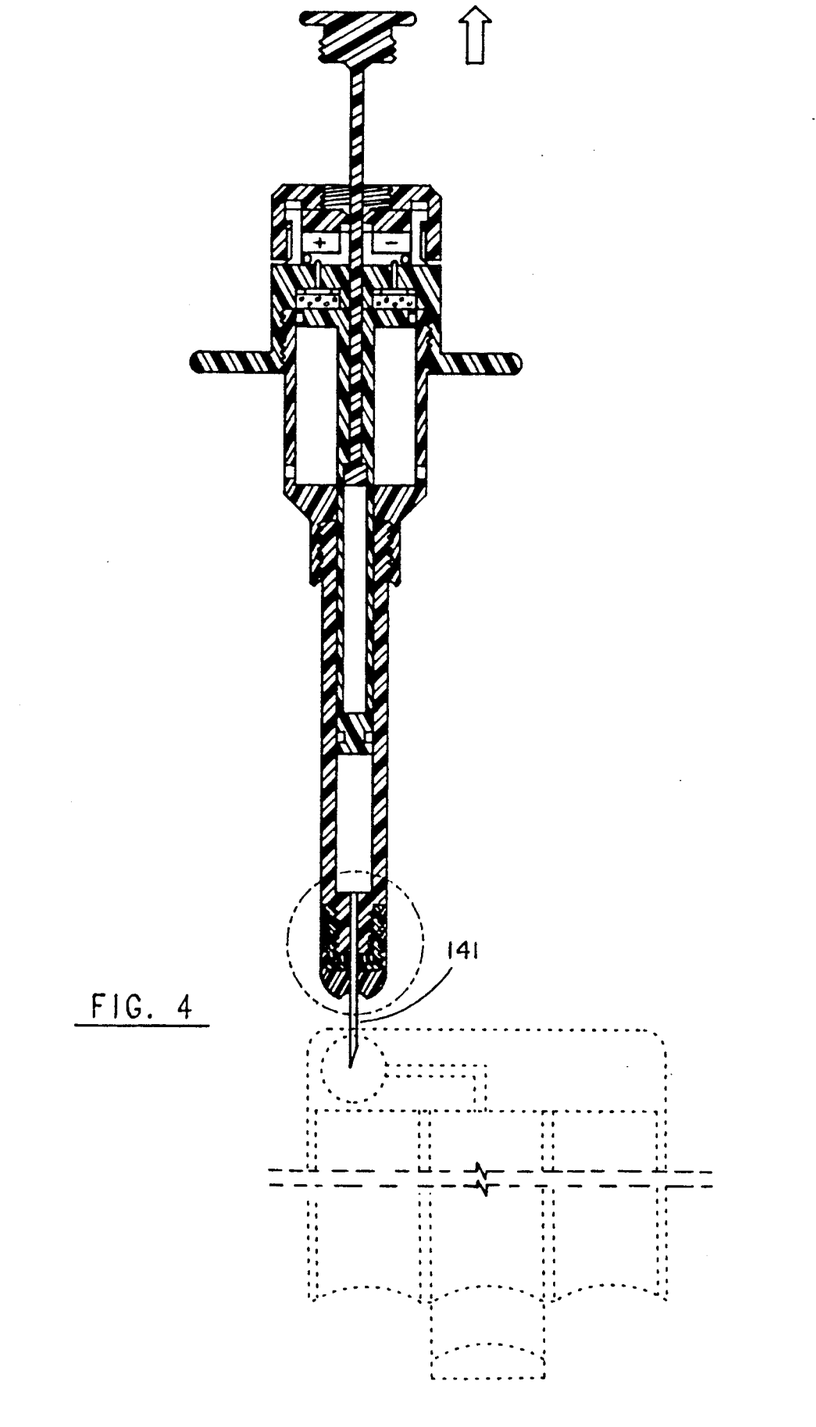
FIG. 4 is a sectional view of the syringe of the present invention illustrating filling of the syringe with medication by passing a filling needle through the septum.

The syringe cartridge may be a preloaded cartridge or may be a reusable cartridge which can be repeatedly filled as illustrated in FIG. 4. In any event, the cartridge 36 includes an injection nozzle 40 which is attached to the cartridge in a suitable manner such as by mating threads 42, 44 on the nozzle and the cartridge. The injection nozzle includes a septum 46 and a septum cap 48 as well as a cannula 50. Thus, as piston 26 is reciprocated mechanically in piston chamber 20 utilizing stem 60 as more fully discussed below, the cartridge 36 may be filled with medication (see FIG. 4).

The proximal end 22 of the piston housing 20 is provided with a power cap indicated generally as 52. In preferred form, the power cap 52 includes a reagent housing 54 having a top cap 56 attached thereto. The power cap 52 is disconnectably connected to the piston housing and contains a reagent 51 such as hydrogen peroxide, or sodium nitrate disks in solid form located in chamber 53 the power cap. The reagent can be rapidly converted into gas when subjected to electric current. The expanding gas will drive piston 26 down the piston chamber 20 and the stopper 32 will expel medication from the medication cartridge 36. Thus, the reagent is positioned in the power cap 52 in a chamber 53 adjacent to the proximal end 22 of the piston housing 20. The power cap 52 is disconnectably connected to the piston housing 20 so that the reagent may be replaced after a use.

A means for converting the reagent to gas to power to syringe is located in the power cap 52. Suitable batteries, such as 1.5 volt watch batteries, 61 and 63 are positioned to be able to contact electrodes 65 and 67 when it is deserved to actuate the syringe. A rubber standoff device 73 is utilized to prevent accidental activation of the syringe. The power cap has a central opening adapted to receive a stem 60 in slidable sealing relationship. Thus, in preferred form, the top cap 56 has a central bore 62 through which a stem 60 passes. A suitable o-ring 64 provides a seal for the stem. The reagent housing 54 also has a central opening to accommodate stem 60. The distal end 66 of the stem 60 is provided with threads 68 which mate with threads 71 on the interior of the elongated portion 30 of the piston 26. Thus, the stem 60 is disconnectably connectable to the piston by rotating the stem to engage or disengage the threads. When the threads are engaged, the stopper 32 of the elongated portion 30 of the piston 26 may be reciprocated by pushing or pulling on handle 70 of the stem in a normal manner. When the threads are disengaged, the piston 26 may be driven down the piston chamber by the rapid expansion of gas in the piston housing.

Figure 1:
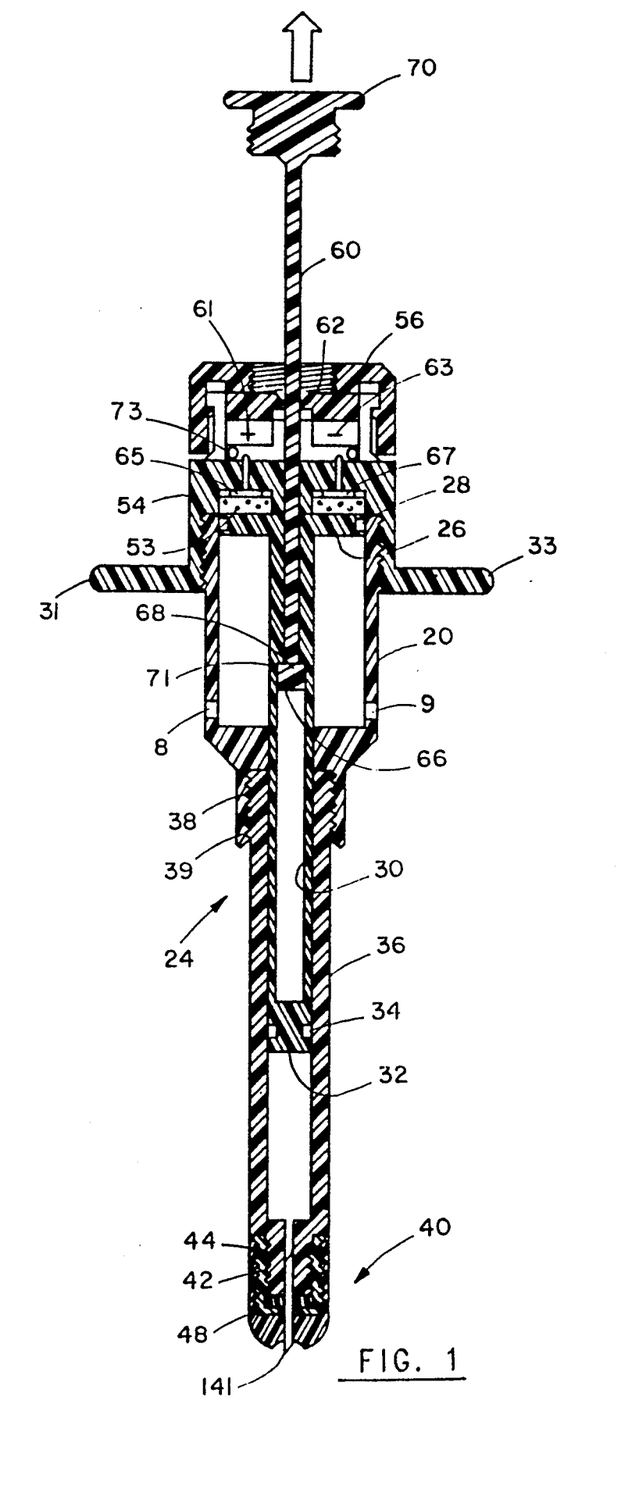
FIG. 1 is a sectional view of the syringe of the present invention in the process of being filled with medication.

With particular reference to FIGS. 1 and 4, the syringe cartridge is loaded with medication by first connecting the stem 60 to the piston by engaging threads 68 and 71. The stem is then pulled out of the proximal end of the piston housing to raise the piston 26 and the piston extension 30 up the piston housing and the syringe cartridge respectively. In this manner, mediation may be drawn into the syringe cartridge.

Figure 2:
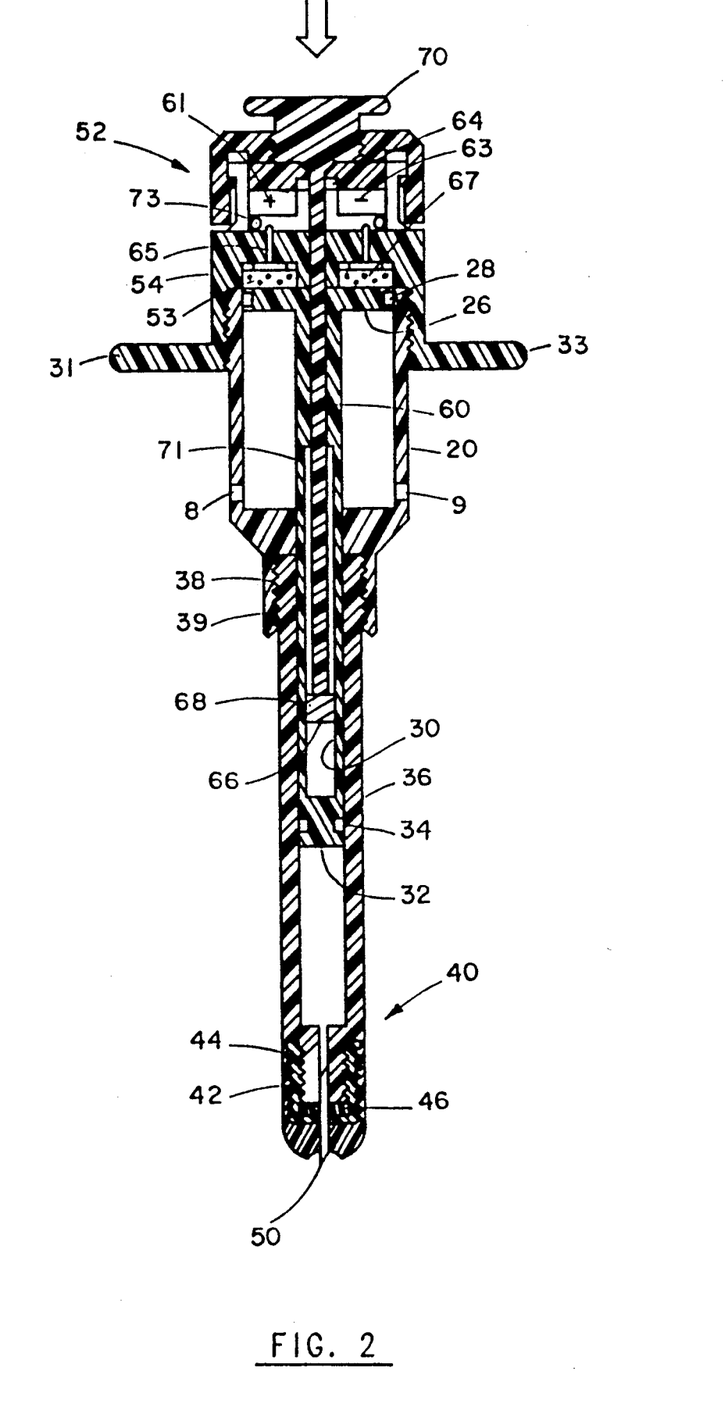
FIG. 2 is a sectional view of the syringe of the present invention in a position ready for injection.

After the syringe cartridge has been filled with proper amount of medication the stem 60 is rotated to disengage threads 68, 71 and the stem 60 and stem handle 70 are pushed back into the syringe and locked to the power cap by mating threads as illustrated in FIG. 2. The syringe is now ready to make an injection utilizing high pressure gas.

Figure 3:
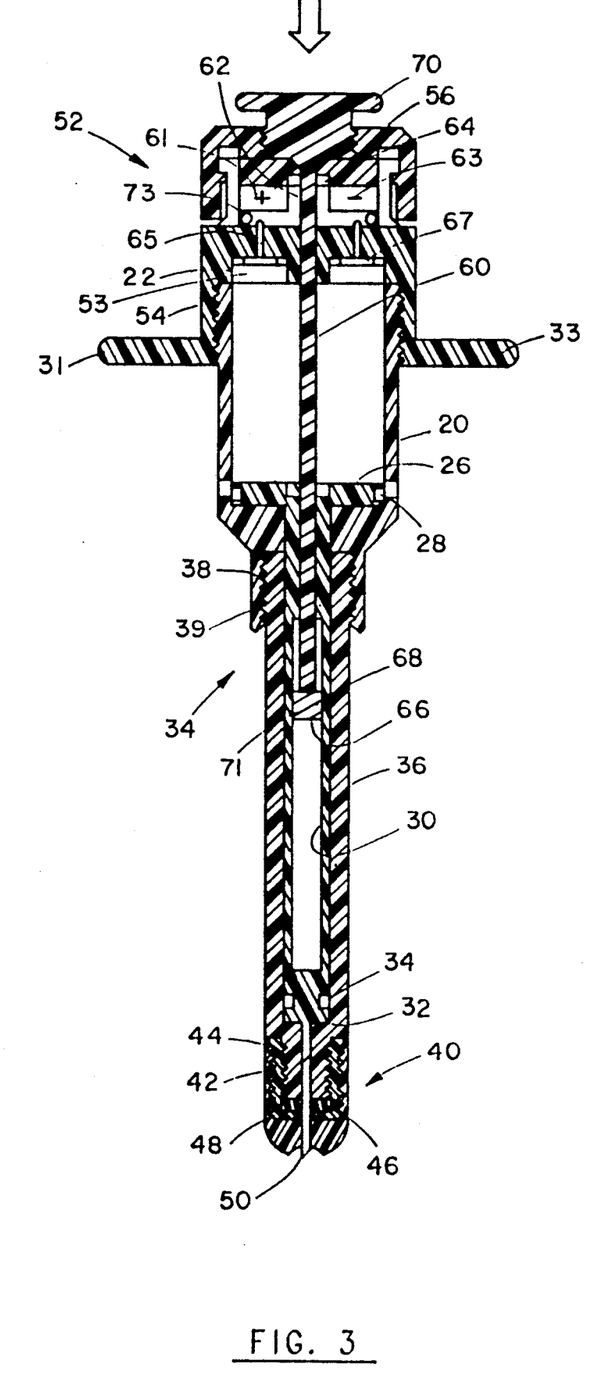
FIG. 3 is a sectional view of the syringe of the present invention after injection has taken place.

When it is desired to make the injection, the injection nozzle 40 is placed firmly against the skin and the power cap is activated by squeezing stem handle 70 towards finger elements 31, 33 to contact electrodes 65, 67 with batteries 61, 63. The resulting current initiates gassification of the reagent in chamber 53. The high pressure gas drives the piston 26 down the piston chamber 20 causing the stopper 32 on the elongated portion 30 of the piston to expel the medication from the syringe cartridge. This is best illustrated in FIG. 3.

Figure 5:
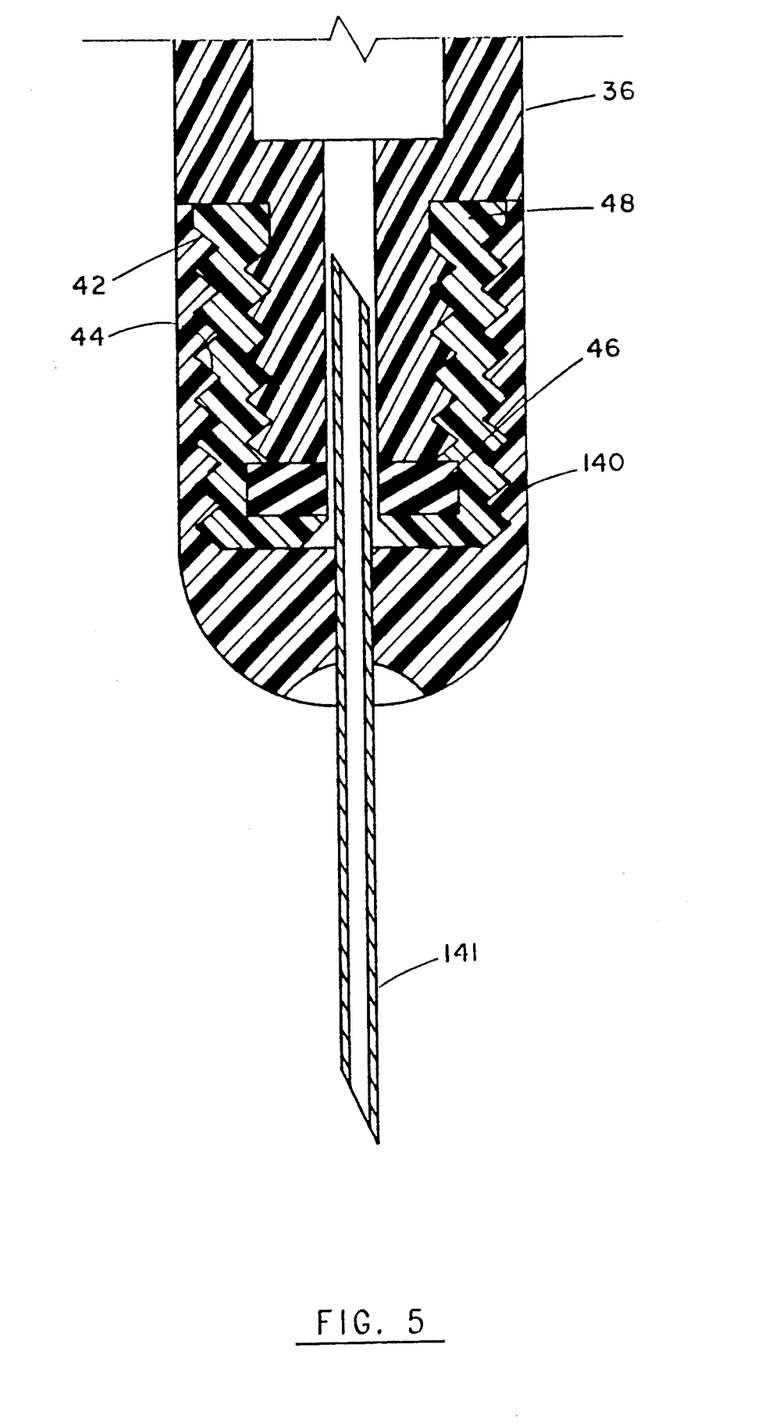

A desirable feature of the present invention is the variety of injection nozzles which may be used with the syringe. As shown in FIG. 4 and as better illustrated in more detail in FIG. 5, which is an enlarged portion circled in FIG. 4, an injection nozzle 140 which is particularly adapted for use when the medication is being withdrawn from a vial or from a device which pre mixes the medication. A standard two ended needle 141 is positioned through a rubber septum 46 to give access to the syringe cartridge 36. A septum cap 48 holds the septum 46 in place. Injection nozzle 140 is screwed onto septum cap 48 and the needle 141 pieces septum 46 to provide access to the syringe cartridge 36. As illustrated in FIG. 4, when it is desired to load the syringe cartridge 36 with medication from a vial or device which premixes the medication, the needle 141 is inserted into the vial or device. Stem 60 is connected to the piston by rotating the stem to engage threads 68, 71. The medication can be drawn into the syringe cartridge 36 by lifting handle 70 as shown in FIG. 4. Alternatively, of course the syringe 36 may be filled by a piston means forcing the medication into the syringe cartridge.

Figure 6:
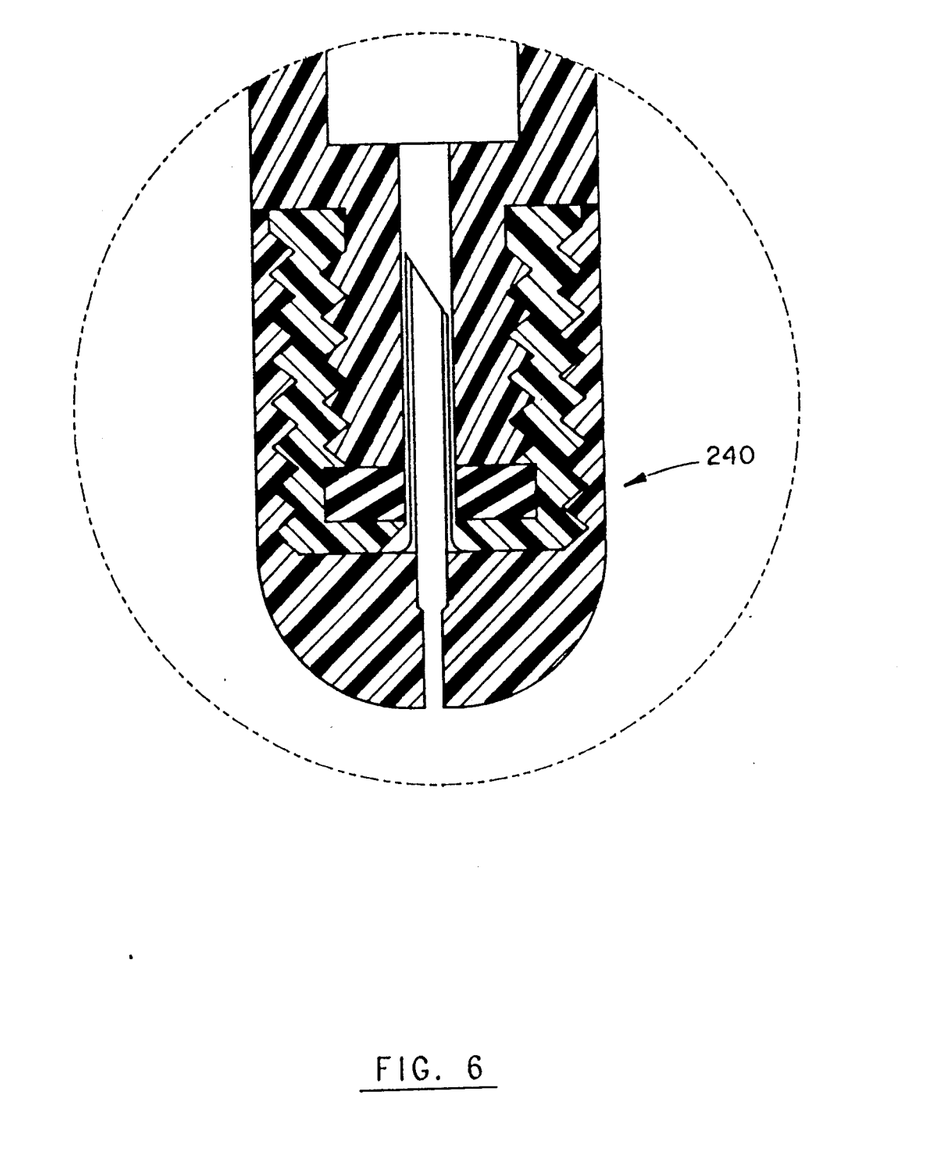
FIG. 6 is a sectional view of a needleless injection nozzle useful in accordance with the present invention.

A needleless version of an injection nozzle 240 is illustrated in FIG. 6. The nozzle is attached to the distal end of the syringe cartridge and includes a rubber septum 46 and a septum cap 48. This version of the nozzle is preferably used with preloaded cartridges, which may be accomplished as described above. Standard pre-loaded cartridges are also useful in this embodiment of the invention.

Figure 7:
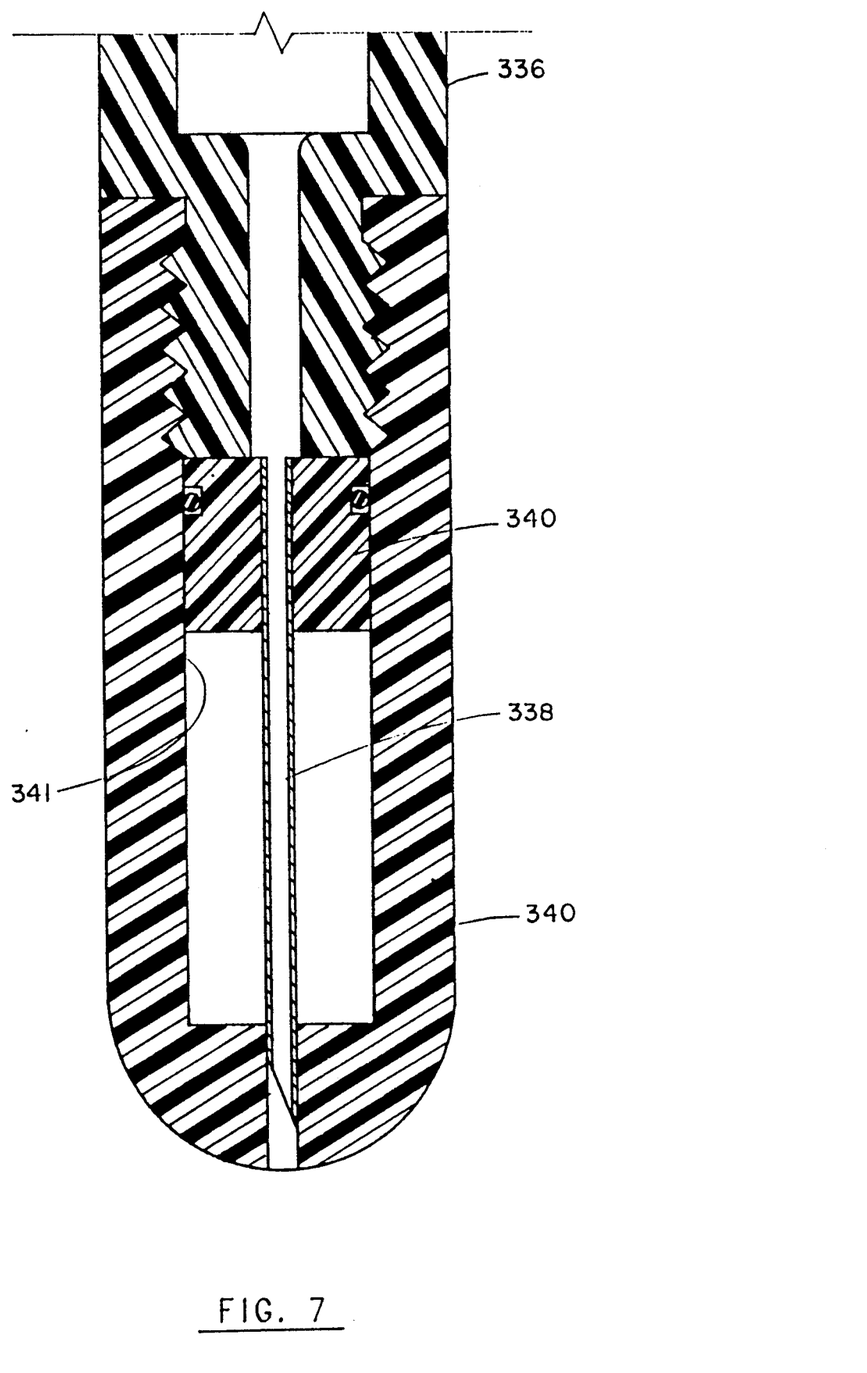
FIG. 7 is a sectional view of another injection nozzle containing a traveling needle in accordance with the invention.

Another version of an injection nozzle for use with the present invention is illustrated in FIG. 7. As is shown the injection nozzle 340 is screwed into the lower end of syringe cartridge 36. A canula 338 is located in the central bore 337 of the nozzle and is attached to a cannula piston 340. The cannula piston 340 is initially recessed in piston chamber 341. When an injection is accomplished, the force of the liquid pharmaceutical leaving the syringe cartridge as indicated by the arrows in FIG. 7 drives the cannula piston 340 and the cannula down the piston chamber to drive the needle into tissue to thus accomplish the injection.

Figure 8:
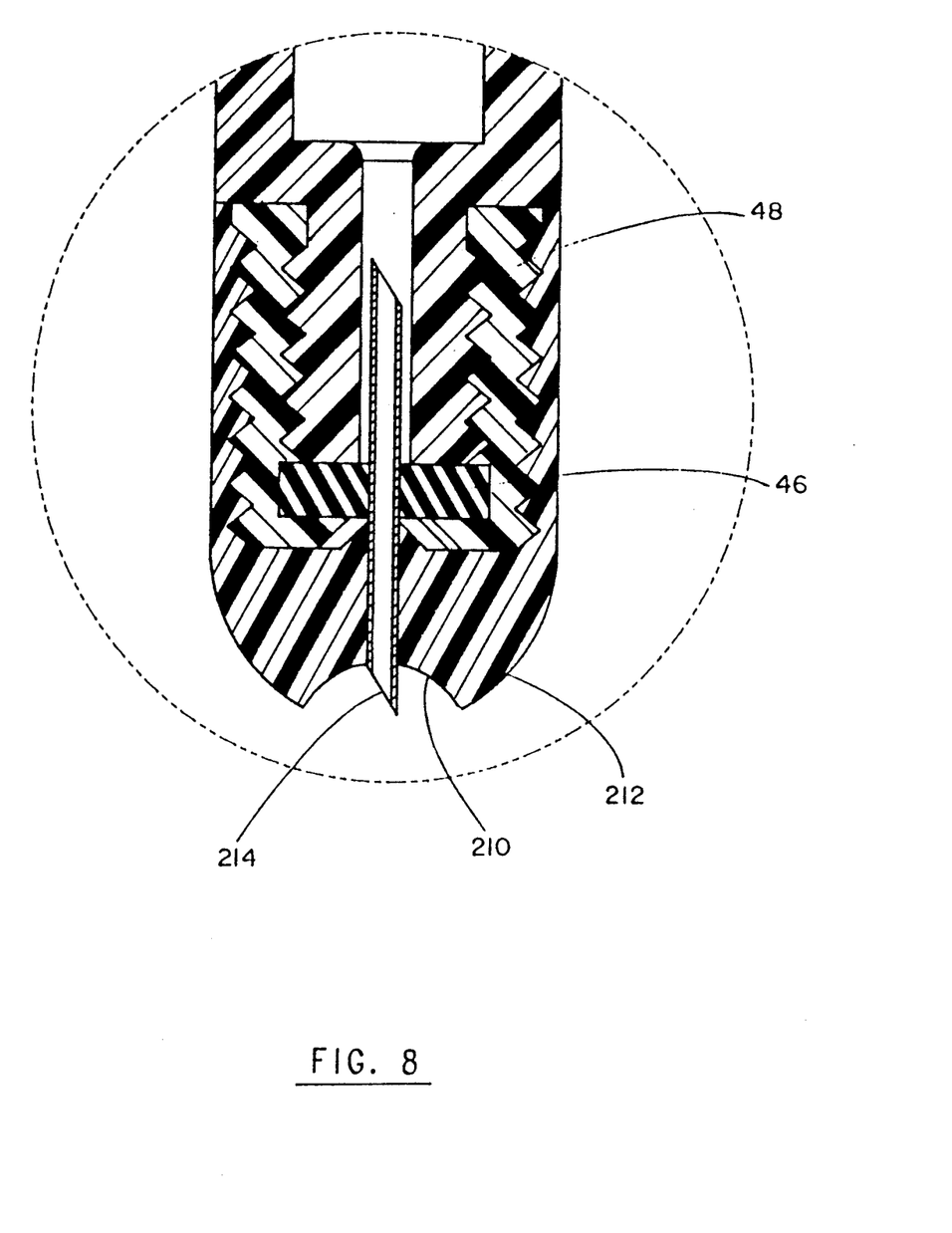
FIG. 8 is a sectional view of another injection nozzle containing a needle which extends out of the nozzle only for enough to barely penetrate the skin.

FIG. 8 illustrates still another injection nozzle. A hollow needle 210 extends out of the end 212 of the nozzle only for enough to barely puncture the skin less than 2 mm. of a person being injected. The lower end 212 of the short injection nozzle is cup shaped as indicated at 214. The interaction of the cup and the skin tends to raise the skin when the syringe is positioned for an injection. When the skin surface is so punctured it is not so intimidating to a person but has the effect of reducing the pressure needed to inject compared to the needleless injector.

It will be apparent that while certain embodiments of the present invention have been shown and described in detail, various changes may be made without departing from the spirit of the present invention. The invention is meant to include all embodiments coming within the scope of the appended claims.

What is claimed is:

1. A syringe comprising a piston housing having distal and proximal ends; a piston in said piston housing adapted for reciprocal movement therein, said piston having a central opening and a co-axially aligned elongated tubular portion extending out of the lower end of said piston housing adapted to be inserted into a syringe cartridge to expel medication therefrom, a power cap on the proximal end of said piston housing having a central opening; a step passing through the central opening in said power cap and the central opening in said piston, said stem being disconnectably connectable to said piston for moving said piston in said piston housing; a reagent means which can be rapidly converted to gas located in said power cap adjacent to the proximal end of said piston housing for driving said piston down said piston chamber; and a means for activating said reagent means to gas when said stem is disconnected from said piston.

2. A syringe comprising a piston housing having distal and proximal ends; a syringe cartridge attached to the distal end of said piston housing, an injection tip disconnectably connected to said syringe cartridge, a piston in said piston housing adapted for reciprocal movement therein, said piston having a central opening and an elongated portion extending out of the distal end of said piston housing into said syringe cartridge and adapted to expel medication therefrom, a power cap on the proximal end of said piston housing having a central opening; a stem passing in sealing engagement through the central opening in said power cap and the central opening in said piston, said stem being disconnectably connectable to said piston for moving said piston in said piston housing and the elongated portion in aid syringe cartridge; a reagent means located in said power cap adjacent to the proximal end of said piston housing for driving said piston down said piston chamber and the elongated portion down said syringe cartridge to eject medication therefrom; and activating means for converting said reagent to gas when said stem is disconnected from said piston.

3. The syringe of claim 2 further characterized in that said injection tip is needleless.

4. The syringe of claim 2 further characterized in that said injection tip includes a hollow needle which is initially recessed in the bore of said injection tip and forced out of said injection tip as medication is ejected from the syringe cartridge to penetrate the skin of a patient to facilitate injection of medication.

5. The syringe of claim 2 further characterized in that said activating means includes a battery in said power cap and electrodes contactable with said battery to provide an electric current to convert said reagent to gas.

6. The syringe of claim 2 further characterized in that the diameter of the piston in the piston housing is at least three times the diameter of the elongated portion.

7. The syringe of claim 2 further characterized in that the syringe cartridge, the piston and the elongated portion are co-axially aligned.

8. The syringe of claim 2 wherein said injection tip includes a hollow needle which extends out of the injection tip to barely penetrate the skin not more than 2 mm.

9. The syringe of claim 5 further characterized in that said battery and said electrodes are contacted by squeezing finger elements positioned on said piston housing.

10. A method of giving an injection to a person comprising connecting a syringe cartridge to the distal end of a syringe, disconnectably connecting a syringe stem to a piston located in a piston housing of the syringe, loading the syringe cartridge with medication by extending the syringe stem out of the proximal end of the piston housing, disconnecting the syringe stem from the piston, placing the syringe against the desired location of the person to be injected, causing gas to expand in the piston housing to drive the piston toward the loaded syringe cartridge whereby medication is expelled from the cartridge and injected into the desired location of the person to be injected.

11. The method of claim 10 further characterized by disconnectably connecting an injection nozzle to the syringe cartridge.

12. The method of claim 10 further characterized in that prior to injecting the medication into the person the skin of the person is slightly penetrated and the injection of medication enters the penetration.

13. The method of claim 10 further characterized in that prior to injecting the medication into the person the skin of the patient is cupped to better assist a needleless injection.

14. The method of claim 10 further including the stop of returning the syringe stem down into the proximal end of the syringe and locking it in place prior to giving the injection.

* * * * *